(12) United States Patent
Suzuki

(10) Patent No.: US 11,440,896 B2
(45) Date of Patent: Sep. 13, 2022

(54) AMINOALKYL COMPOUND

(71) Applicant: Daiichi Sankyo Company, Limited, Tokyo (JP)

(72) Inventor: Keisuke Suzuki, Tokyo (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 275 days.

(21) Appl. No.: 16/965,972

(22) PCT Filed: Feb. 5, 2019

(86) PCT No.: PCT/JP2019/004071
§ 371 (c)(1),
(2) Date: Jul. 29, 2020

(87) PCT Pub. No.: WO2019/156074
PCT Pub. Date: Aug. 15, 2019

(65) Prior Publication Data
US 2021/0040057 A1 Feb. 11, 2021

(30) Foreign Application Priority Data
Feb. 6, 2018 (JP) .............. JP2018-018940

(51) Int. Cl.
*A61K 31/351* (2006.01)
*C07D 309/06* (2006.01)
*A61P 29/00* (2006.01)
*A61K 9/70* (2006.01)

(52) U.S. Cl.
CPC .......... *C07D 309/06* (2013.01); *A61K 9/7023* (2013.01); *A61P 29/00* (2018.01)

(58) Field of Classification Search
CPC .. C07D 309/06; C07D 309/04; C07D 309/08; A61K 9/7023; A61K 9/7053; A61K 9/70; A61K 31/351; A61P 29/00; A61P 25/04; A61P 35/00
USPC ........................................................ 514/459
See application file for complete search history.

(56) References Cited

U.S. PATENT DOCUMENTS 5,733,936 A 3/1998 Buschmann et al.

FOREIGN PATENT DOCUMENTS

JP 9-31033 A 2/1997

OTHER PUBLICATIONS

International Search Report dated Apr. 23, 2019, issued in corresponding Application PCT/JP2019/004071, filed Feb. 5, 2019, 1 page.
Eiden, F., et al., "ZNS active phenylpyrans: 3-(dimethylaminomethyl)-4-(3-methoxyphenyl)tetrahydro-4-pyranol and-4-thiopyranol," Archiv der Pharmazie, 320:1099-1103, 1987.

*Primary Examiner* — Taylor V Oh
(74) *Attorney, Agent, or Firm* — Christensen O'Connor Johnson Kindness PLLC

(57) ABSTRACT

The present invention directs to provide a novel compound for treating and/or preventing pain, having excellent skin permeation and reduced skin irritation. The present invention provides a compound of formula (I) or a pharmaceutically acceptable salt thereof ($R^1$: a methyl group or other like group, $R^2$: a fluorine atom or other like group, $R^3$: a methyl group or other like group, $R^4$: a methyl group or other like group, $R^5$: a methyl group or other like group)

[Formula 1]

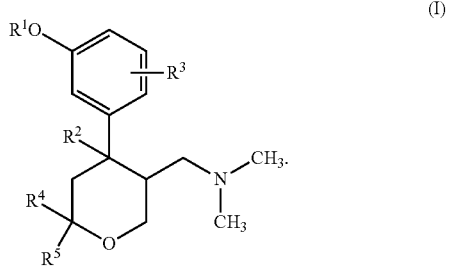

(I)

26 Claims, No Drawings

AMINOALKYL COMPOUND

TECHNICAL FIELD

The present invention relates to a novel compound, a salt thereof, or a hydrate thereof used to treat and/or prevent pain, having excellent skin permeation and reduced skin irritation, and further relates to a patch containing the compound.

BACKGROUND ART

A percutaneous absorption type preparation is a preparation intended to deliver an active ingredient through the skin to the systemic circulatory blood stream. Features of percutaneous absorption type preparations include being non-invasive, persistent, undergoing no first-pass effect, being able to visually observe dosing status, and being easy to interrupt the dosing (Non Patent Literature 1).

Percutaneous absorption type preparations mainly employ a method that requires a penetration enhancing technique that makes a change in the barrier function of the stratum corneum, or a method that formulates a compound capable of being absorbed percutaneously into a percutaneous absorption patch. Examples of methods that requires a penetration enhancing technique include a method with a penetration enhancer, and a method by structurally breaking down the stratum corneum, for example, with a microneedle. However, since these methods are skin irritating, side effects such as applied site pruritus and applied site erythema have been reported (Non Patent Literatures 2 to 5).

When the amount of a penetration enhancer exceeds an upper limit, skin irritation tends to be enhanced, which can cause redness, edema, or the like. The method that formulates a compound into a percutaneous absorption patch, which uses little or no penetration enhancer or the like, has been mainly used by altering the route of administration of drugs that are difficult to administer orally or the like.

Since such studies on existing medicines that can be absorbed percutaneously have been carried out extensively for a long time, it is said that it will be difficult to find a new compound in such a way in the future. For a new patch, it is expected to design a compound that has percutaneous absorption ability by new synthetic development focusing on, for example, the physical properties necessary for absorption.

There are several patches currently in clinical use for treating cancer pain and chronic non-cancer pain. Such patches, while exhibiting potent medicinal effects, often have side effects such as vomiting, nausea and constipation. Side effects such as itching and erythema occurring at the applied site have also been reported (Non Patent Literatures 6 to 8), because a percutaneous penetration enhancer is often used in patches since the skin permeation of the main drug is generally low.

In addition, many analgesic drugs currently in clinical use do not exhibit skin permeation due to their structure, physical properties, or the like, and are used in administration methods for oral agents, injectables and the like (Non Patent Literature 9 to 11). Novel compounds suitable for patches, which are as effective as analgesic drugs used as oral agents, injectables, or the like, are needed as a medicine that broadens the range of options for the treatment and/or prevention of pain.

Faxeladol, the compound 3-[(1R,2R)-2-[(dimethylamino)methyl]cyclohexyl]phenol) represented by the following formula, is known as an orally applicable medicine having analgesic action (Patent Literature 1).

[Formula 1]

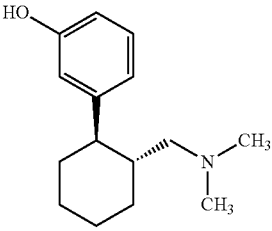

CITATION LIST

Patent Literature

Patent Literature 1: Japanese Translation of PCT International Application Publication No. 2009-507875

Non Patent Literature

Non Patent Literature 1: British Journal of Pharmacology (2015) 172, 2179-2209.

Non Patent Literature 2: Am J Clin Dermatol 2000: 1: 361-368

Non Patent Literature 3: Ther Deliv. 2010 Jul; 1 (1): 109-131.

Non Patent Literature 4: Clinical, Cosmetic and Investigational Dermatology 2017:10 289-298.

Non Patent Literature 5: Dermatol Surg 2017;0:1-8.

Non Patent Literature 6: Curr Med Res Opin. 2006 March; 22 (3):501-509.

Non Patent Literature 7: Cutan Ocul Toxicol. 2010 December; 29(4):241-246.

Non Patent Literature 8: Contact Dermatitis. 2008 December; 59 (6):366-369.

Non Patent Literature 9: Molecules 2018, 23, 681.

Non Patent Literature 10: Health, Labor and Welfare Policy Grants (Research on Chronic Pain), "Research on Constructing a System for the Treatment and Education of Chronic Pain Problems" Study Group (supervision), Working Group for Preparation of Clinical Practice Guideline for Chronic Pain (ed.), "Clinical Practice Guideline for Chronic Pain", Publication Department of Medical Books, Shinko Trading Co., Ltd., Apr. 5, 2018

Non Patent Literature 11: General Hospital Psychiatry 31 (2009) 206-219.

SUMMARY OF INVENTION

Technical Problem

The present inventors have synthesized and intensively studied a wide range of novel compounds, and as a result have found that the compound of the present invention is a compound that has reduced side effects, exhibits strong analgesic action, has good pharmacokinetics and solubility, and has skin permeation without skin irritation, and have thus completed the present invention.

Solution to Problem

Specifically, the present invention is as described below.
[1] A compound of formula (I) or a pharmaceutically acceptable salt thereof:

[Formula 2]

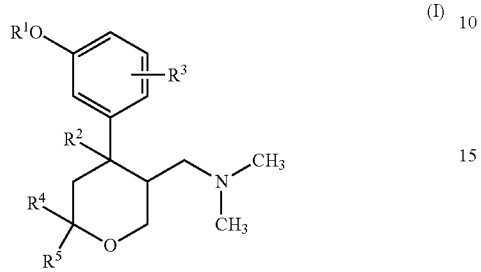

(I)

wherein each symbol has the following meaning:
$R^1$ is a hydrogen atom or a methyl group;
$R^2$ is a hydrogen atom or a fluorine atom;
$R^3$ is a hydrogen atom or a methyl group;
$R^4$ is a hydrogen atom or a methyl group; and
$R^5$ is a hydrogen atom or a methyl group.
[2] The compound according to [1] or a pharmaceutically acceptable salt thereof, wherein $R^1$ is a hydrogen atom.
[3] The compound according to [1] or [2] or a pharmaceutically acceptable salt thereof, wherein $R^2$ is a hydrogen atom.
[4] The compound according to any one of [1] to [3] or a pharmaceutically acceptable salt thereof, wherein $R^3$ is a hydrogen atom.
[5] The compound according to any one of [1] to [4] or a pharmaceutically acceptable salt thereof, wherein $R^4$ and $R^5$ are hydrogen atoms.
[6] The compound according to [1] or a pharmaceutically acceptable salt thereof, wherein the compound of formula (I) is any one of the compounds shown below:
3-[(3R*,4R*)-3-(Dimethylaminomethyl)tetrahydropyran-4-yl]phenol;
3-[(4R*,5R*)-5-(Dimethylaminomethyl)-2,2-dimethyltetrahydropyran-4-yl]phenol;
3-[(3R*,4R*)-3-(Dimethylaminomethyl)tetrahydropyran-4-yl]-5-methylphenol;
3-[(3R*,4R*)-3-(Dimethylaminomethyl)tetrahydropyran-4-yl]-2-methylphenol;
3-[3-Dimethylaminomethyl-4-fluorotetrahydropyran-4-yl]-phenol.
[7] The compound shown below or a pharmaceutically acceptable salt thereof:
3-[(3R*,4R*)-3-(Dimethylaminomethyl)tetrahydropyran-4-yl]phenol.
[8] The compound shown below or a pharmaceutically acceptable salt thereof:
3-[(3R,4R)-3-(Dimethylaminomethyl)tetrahydropyran-4-yl]phenol.
[9] A pharmaceutical composition comprising the compound according to any one of [1] to [8] or a pharmaceutically acceptable salt thereof as an active ingredient.
[10] The pharmaceutical composition according to [9], wherein the composition is in the form of a patch.
[11] The pharmaceutical composition according to [9] or [10], for treating and/or preventing pain.
[12] The compound according to any one of [1] to [8] or a pharmaceutically acceptable salt thereof, for use in the treatment and/or prevention of pain.
[13] The pharmaceutical composition according to [11], wherein the pain is cancer pain and/or chronic non-cancer pain.
[14] A method for treating and/or preventing pain, comprising administering an effective amount of the pharmaceutical composition according to [9] or [10].

Advantageous Effects of Invention

Since the compound of the present invention or a pharmaceutically acceptable salt thereof, having a specific chemical structure, has different properties in various aspects from those of known analgesics, the compound or a pharmaceutically acceptable salt thereof is considered to be useful as a novel medicine.

The compound of the present invention and pharmaceutically acceptable salts thereof have excellent properties in terms of analgesic activity, bioavailability, in vitro activity, in vivo activity, rapid onset of drug efficacy, sustained drug efficacy, physical stability, drug interaction, toxicity or the like, and are useful as a medicine. Furthermore, the compound of the present invention and pharmaceutically acceptable salts thereof have excellent solubility in a composition employed in a patch, attained by optimizing the molecular weight, fat solubility, and the like, and furthermore have excellent skin permeation. Thus, the compound of the present invention and pharmaceutically acceptable salts thereof are useful since they exert an excellent effect when used as a patch.

DESCRIPTION OF EMBODIMENTS

Hereinafter, the present invention is described in detail.
Suitable aspects of the present invention are as described below.

A compound of formula (I) or a pharmaceutically acceptable salt thereof:

[Formula 3]

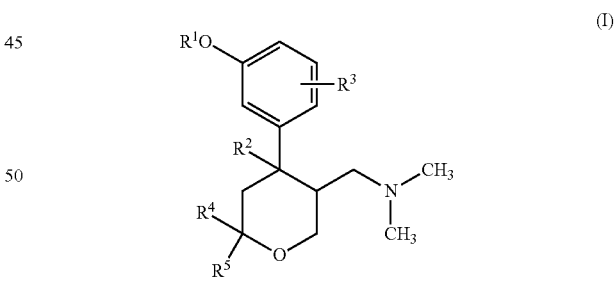

(I)

wherein each symbol has the following meaning:
$R^1$ is a hydrogen atom or a methyl group;
$R^2$ is a hydrogen atom or a fluorine atom;
$R^3$ is a hydrogen atom or a methyl group;
$R^4$ is a hydrogen atom or a methyl group; and
$R^5$ is a hydrogen atom or a methyl group.

A particularly preferred aspect of the present invention is a compound described in the Example or a pharmaceutically acceptable salt thereof.

The compounds of the present invention are generally named according to the nomenclature of the International Union of Pure and Applied Chemistry (IUPAC).

In the compound name of the present invention, if the structure of the compound has an atom that is an asymmetric center, its absolute configuration may be indicated by R and S (written with position number).

The relative configuration may be indicated by placing a star (R* and S*) on the configuration indication when the asymmetric center configuration is initially described as R or S, or by placing a prefix (symbol) rel- (meaning relative) before the name.

A racemic mixture is generally indicated without, in particular, R and S for its absolute configuration, although it is sometimes indicated with a symbol RS or SR instead of R* or S*, or by placing a prefix (symbol) rac- (meaning racemic) before the name.

The term "pharmaceutically acceptable salt thereof" refers to a salt which can be used as a medicine.

The compound of the present invention or a pharmaceutically acceptable salt thereof may absorb water or adsorb moisture or form a hydrate when it is left in the air or by re-crystallization. Various hydrates, solvates and polymorphic compounds are also included in the present invention.

The compound of the present invention, a pharmaceutically acceptable salt thereof, or a solvate thereof may have various types of isomers such as a geometric isomer, e.g., a cis isomer or a trans isomer, a tautomer, and an optical isomer, e.g., a d-form or an l-form, depending on the type and combination of substituents. Unless otherwise specified, all of the isomers, stereoisomers, and mixtures of these isomers and stereoisomers in any ratio are also included in the compound. A mixture of these isomers can be separated by a known separation means.

A labeled form of the compound, more specifically, a compound in which one or more atoms of the compound are replaced with an isotope (for example, 2H, 3H, 13C, 14C, 35S), is also included in the compound of the present invention.

The compound of formula (I) of the present invention can be produced according to Method A or Method B described below.

The solvent used in the reaction of each step of Method A or Method B below is not particularly limited as long as it does not inhibit the reaction and to some extent dissolves the starting materials, and, for example, is selected from the following solvent groups.

The solvent groups include: hydrocarbons such as pentane, n-hexane, octane, petroleum ether, ligroin, cyclohexane; amides such as formamide, N,N-dimethylformamide, N,N-dimethylacetamide, N-methyl-2-pyrrolidone, N-methyl-2-pyrrolidinone, hexamethyl phosphate triamide; ethers such as diethyl ether, diisopropyl ether, tetrahydrofuran, 1,4-dioxane, 1,2-dimethoxyethane, diethylene glycol dimethyl ether, cyclopentylmethyl ether; alcohols such as methanol, ethanol, n-propanol, i-propanol, n-butanol, 2-butanol, 2-methyl-1-propanol, t-butanol, isoamyl alcohol, diethylene glycol, glycerin, octanol, cyclohexanol, methyl cellosolve; sulfoxides such as dimethyl sulfoxide; sulfones such as sulfolane; nitriles such as acetonitrile, propionitrile, butyronitrile, isobutyronitrile; esters such as ethyl formate, ethyl acetate, propyl acetate, butyl acetate, diethyl carbonate; ketones such as acetone, methyl ethyl ketone, 4-methyl-2-pentanone, methyl isobutyl ketone, isophorone, cyclohexanone; nitro compounds such as nitroethane, nitrobenzene; halogenated hydrocarbons such as dichloromethane, 1,2-dichloroethane, chlorobenzene, dichlorobenzene, chloroform, carbon tetrachloride; aromatic hydrocarbons such as benzene, toluene, xylene; carboxylic acids such as acetic acid, formic acid, propionic acid, butyric acid, trifluoroacetic acid; amines such as N-methylmorpholine, triethylamine, tripropylamine, tributylamine, diisopropylethylamine, dicyclohexylamine, N-methylpiperidine, pyridine, 2,6-lutidine, 4-pyrrolidinopyridine, picoline, 4-(N,N-dimethylamino)pyridine, 2,6-di(t-butyl)-4-methylpyridine, quinoline, N,N-dimethylaniline, N,N-diethylaniline, 1,5-diazabicyclo[4.3.0]nona-5-ene (DBN), 1,4-diazabicyclo[2.2.2]octane (DABCO), 1,8-diazabicyclo[5.4.0]undeca-7-ene (DBU), piperidine; water; or a mixture of these solvents.

The base used in the reaction of each step of Method A or Method B below is any one of alkali metal carbonates, such as sodium carbonate, potassium carbonate, lithium carbonate, cesium carbonate; alkali metal hydrogen carbonates such as sodium hydrogen carbonate, potassium hydrogen carbonate, lithium hydrogen carbonate; alkali metal acetates such as sodium acetate, potassium acetate, lithium acetate, cesium acetate; alkali metal hydrides such as lithium hydride, sodium hydride and potassium hydride; alkali metal hydroxides such as sodium hydroxide, potassium hydroxide, barium hydroxide, lithium hydroxide; alkali metal phosphates such as sodium phosphate, potassium phosphate; alkali metal salts such as L-proline sodium, L-proline potassium; inorganic bases such as alkali metal fluorides, e.g., sodium fluoride, potassium fluoride; alkali metal alkoxides such as sodium methoxide, sodium ethoxide, sodium-t-butoxide, potassium-t-butoxide; alkali metal trialkylsiloxides such as sodium trimethylsiloxide, potassium trimethylsiloxide, lithium trimethylsiloxide; organic bases such as N-methylmorpholine, triethylamine, tripropylamine, tributylamine, diisopropylethylamine, dicyclohexylamine, N-methylpiperidine, pyridine, 2,6-lutidine, choridine, 4-pyrrolidinopyridine, picoline, 4-(N,N-dimethylamino) pyridine, 2,6-di(t-butyl)-4-methylpyridine, quinoline, N,N-dimethylaniline, N,N-diethylaniline, 1,5-diazabicyclo[4.3.0]nona-5-ene (DBN), 1,4-diazabicyclo[2.2.2] octane (DABCO), 1,8-diazabicyclo[5.4.0] undeca-7-ene (DBU); alkali metal amides such as lithium diisopropylamide, hexamethyldisilazane lithium, hexamethyldisilazane sodium; and amino acids such as proline.

In the reaction of each step of Method A or Method B below, the reaction temperature varies depending on the solvent, starting material, reagent, or the like, and the reaction time varies depending on the solvent, starting material, reagent, reaction temperature, or the like.

In the reaction of each step of Method A or Method B below, after the reaction is over, each compound of interest is taken from the reaction mixture according to a conventional method. For example, the reaction mixture is appropriately neutralized and, if insoluble matter is present, the mixture is filtered to remove the matter. Then, water and a water-immiscible organic solvent such as ethyl acetate are added, and the resulting organic layer containing the compound of interest is separated, washed with water or the like, and then dried over anhydrous magnesium sulfate, anhydrous sodium sulfate, or the like. After filtration, the solvent is distilled off to obtain the compound of interest. If necessary, the obtained compound of interest can be separated and purified by appropriately combining methods commonly used for isolation and purification of organic compounds, such as recrystallization, reprecipitation, chromatography, and other conventional methods. The chromatography includes, for example, adsorption column chromatography with a carrier such as silica gel, alumina, magnesium-silica gel-based florisil, or SO3H-silica (manufactured by FUJI SILYSIA CHEMICAL LTD.); methods with a synthetic adsorbent such as partition column chromatography with a carrier such as Cephadex LH-20 (manufactured by Pharmacia), Amberlight XAD-11 (manufactured by Rohm and Haas Company), or DIAION HP-20 (manufactured by Mitsubishi Chemical Corporation); ion-exchange chromatography; and normal phase/reverse phase column chromatography with silica gel or alkylated silica gel (preferably, high performance liquid chromatography), some of which are combined as appropriate where the compound of interest is eluted with an appropriate eluent. When the compound of interest is insoluble in a solvent, the compound can be purified by washing the obtained solid crude product with a solvent. The compound of interest in each step can also be used in the next reaction as is without purification.

General Production Method

In the following formula, the description indicating the conformation of the compounds shows the relative configuration of each substituent, but not the absolute configuration of each substituent.

Method A is a method for producing a compound (A8) or (A9) of the present invention.

Method A

[Formula 4]

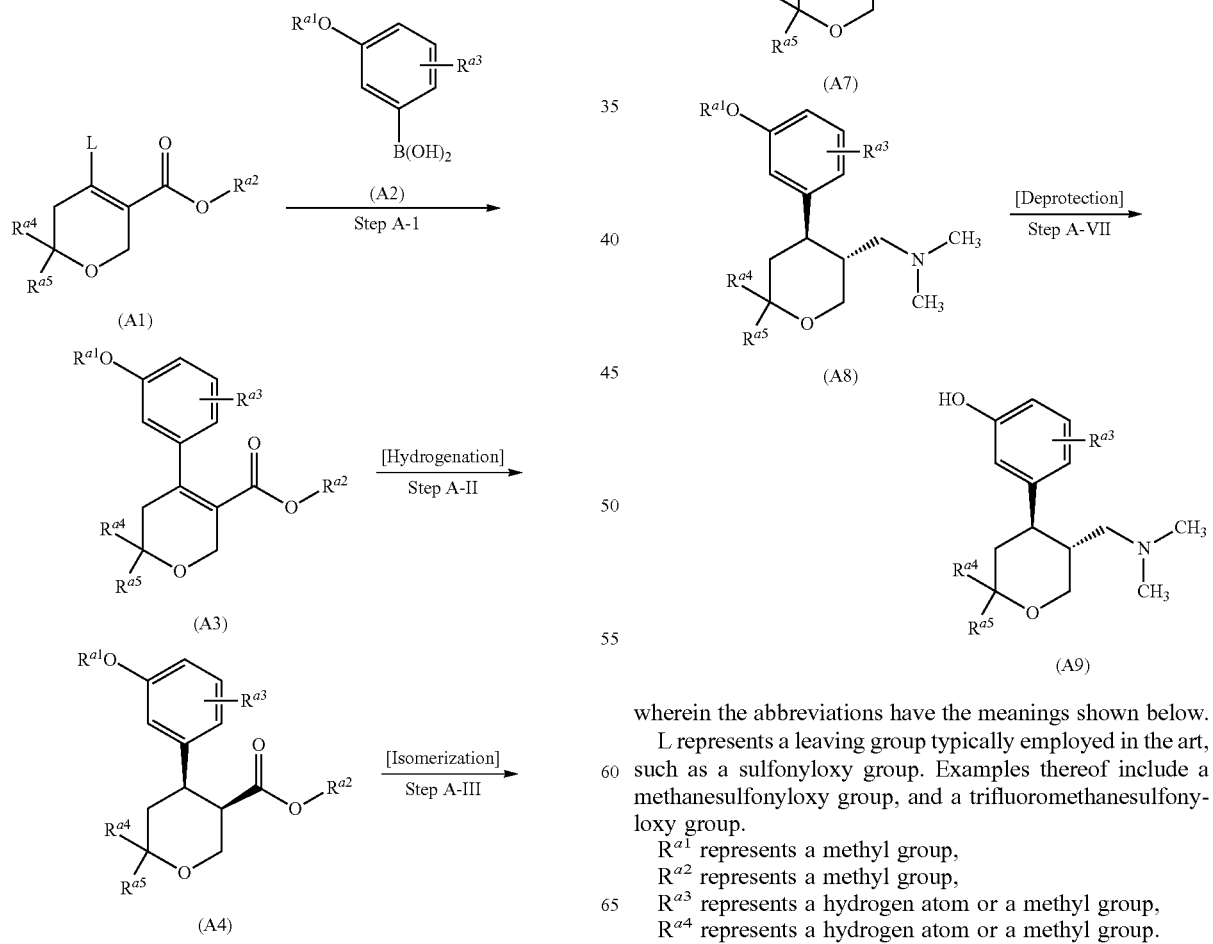

wherein the abbreviations have the meanings shown below.

L represents a leaving group typically employed in the art, such as a sulfonyloxy group. Examples thereof include a methanesulfonyloxy group, and a trifluoromethanesulfonyloxy group.

$R^{a1}$ represents a methyl group,
$R^{a2}$ represents a methyl group,
$R^{a3}$ represents a hydrogen atom or a methyl group,
$R^{a4}$ represents a hydrogen atom or a methyl group.
$R^{a5}$ represents a hydrogen atom or a methyl group.

Step A-I

This step is a step of reacting a compound (A1) with a boric acid compound (A2) in the presence of a base in a solvent to produce a compound (A3).

The solvent used in this step is preferably an amide or an ether, more preferably N,N-dimethylformamide or 1,4-dioxane.

The base used in this step is preferably an alkali metal carbonate, more preferably potassium carbonate.

The reaction temperature in this step is typically 50 to 120° C., preferably 80 to 100° C.

The reaction time in this step is typically 3 to 72 hours, preferably 12 to 48 hours.

This step can be performed under microwave irradiation. The reaction time in this case is typically 10 minutes to 3 hours, preferably 15 to 90 minutes.

Step A-II

This step is a step of hydrogenating a compound (A3) in the presence of palladium carbon in a solvent to produce a compound (A4).

The solvent used in this step is preferably an alcohol, more preferably methanol.

The reaction temperature in this step is typically 20 to 50° C., preferably 20 to 30° C.

The reaction time in this step is typically 1 to 24 hours, preferably 1 to 6 hours.

Step A-III

This step is a step of isomerizing a compound (A4) in the presence of a base in a solvent to produce a compound (A5).

The solvent used in this step is preferably an alcohol, more preferably methanol.

The base used in this step is preferably an alkali metal alkoxide, more preferably sodium methoxide.

The reaction temperature in this step is typically 20 to 100° C., preferably 40 to 70° C.

The reaction time in this step is typically 1 to 24 hours, preferably 20 to 24 hours.

Step A-IV

This step is a step of reacting a compound (A5) with lithium aluminum hydride in a solvent to produce a compound (A6).

The solvent used in this step is preferably an ether, more preferably tetrahydrofuran.

The reaction temperature in this step is typically 0 to 60° C., preferably 0 to 20° C.

The reaction time in this step is typically 1 to 24 hours, preferably 1 to 2 hours.

Step A-V

This step is a step of reacting a compound (A6) with, for example, methanesulfonyl chloride in the presence of a base in a solvent to produce a compound (A7).

The solvent used in this step is preferably a halogenated hydrocarbon, more preferably dichloromethane.

The base used in this step is preferably a tertiary alkylamine, more preferably triethylamine.

The reaction temperature in this step is typically −10 to 0° C., preferably −5 to 0° C.

The reaction time in this step is typically 1 to 24 hours, preferably 12 to 24 hours.

Step A-VI

This step is a step of reacting a compound (A7) with dimethylamine hydrochloride in the presence of a base in a solvent to produce a compound (A8).

The solvent used in this step is preferably an amide or an ether, more preferably N,N-dimethylformamide.

The base used in this step is preferably a tertiary alkylamine, more preferably triethylamine.

The reaction temperature in this step is typically 50 to 120° C., preferably 80 to 100° C.

The reaction time in the step is typically 3 to 72 hours, preferably 12 to 48 hours.

This step can be performed under microwave irradiation. The reaction time in this case is typically 10 minutes to 3 hours, preferably 15 to 90 minutes.

Step A-VII

This step is a step of reacting a compound (A8) with a solution of boron tribromide in methylene chloride in a solvent to produce a compound (A9).

The solvent used in this step is preferably a halogenated hydrocarbon, more preferably dichloromethane.

The reaction temperature in this step is typically −78° C. to 0° C., preferably −78° C. to −40° C.

The reaction time in this step is typically 1 to 24 hours, preferably 12 to 24 hours.

Method B is a method of producing a compound (B5) of the present invention.

Method B

[Formula 5]

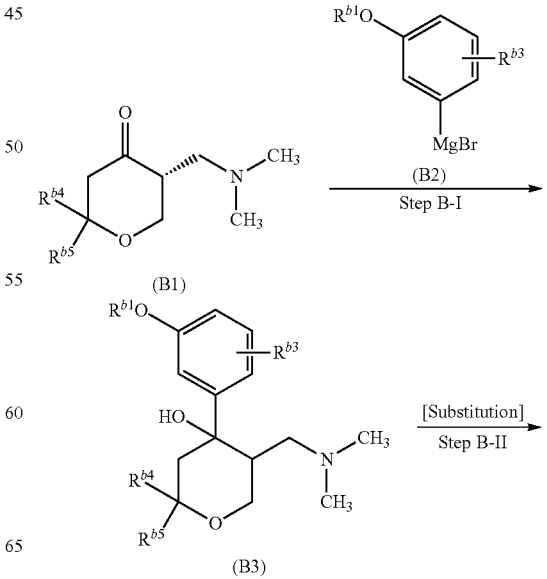

-continued (B4)

(B5)

wherein the abbreviations have the meanings shown below:
$R^{b1}$ represents a methyl group;
$R^{b3}$ represents a hydrogen atom or a methyl group;
$R^{b4}$ represents a hydrogen atom or a methyl group;
$R^{b5}$ represents a hydrogen atom or a methyl group.

Step B-I

This step is a step of reacting a compound (B1) with a magnesium bromide compound (B2) in a solvent to produce. a compound (B3)

The solvent used in this step is preferably an ether, more preferably tetrahydrofuran.

The reaction temperature in this step is typically 0 to 60° C., preferably 0 to 30° C.

The reaction time in this step is typically 1 to 24 hours, preferably 2 to 6 hours.

Step B-II

This step is a step of reacting a compound (B3) with N,N-diethylaminosulfur trifluoride in a solvent to produce a compound (B4).

The solvent used in this step is preferably a halogenated hydrocarbon, more preferably dichloromethane.

The reaction temperature in this step is typically −78° C. to 0° C., preferably −78° C. to −40° C.

The reaction time in this step is typically 1 to 24 hours, preferably 12 to 24 hours.

Step B-III

This step is a step of hydrogenating a compound (B4) in the presence of palladium carbon in a solvent to produce a compound (B5).

The solvent used in this step is preferably an alcohol, more preferably methanol.

The reaction temperature in this step is typically 20 to 50° C., preferably 20 to 30° C.

The reaction time in this step is typically 1 to 24 hours, preferably 1 to 6 hours.

The compound (A1) and the compound (B1) are known compounds or readily produced according to known methods from known starting materials or by similar methods thereto.

The compound of the present invention or a pharmaceutically acceptable salt thereof can be administered in various forms.

The administration thereof may be oral administration in the form of a tablet, a pill, a capsule, a granule, a powder, a solution, or the like, or parenteral administration in the form of an injection such as intraarticular, intravenous, or intramuscular injection, a suppository, an eye drop, an eye ointment, a transdermal liquid, an ointment, a patch, a transmucosal liquid, a transmucosal patch, an inhalant, or the like.

A solid composition for oral administration is used in the form of a tablet, a powder, a granule, or the like. Such a solid composition is produced by mixing one or more active ingredients with at least one inactive excipient such as lactose, mannitol, glucose, hydroxypropyl cellulose, microcrystalline cellulose, starch, polyvinylpyrrolidone and/or magnesium aluminometasilicate.

The composition may contain an inactive additive such as a lubricant, e.g., such as magnesium stearate, a disintegrant e.g., sodium carboxymethyl starch, a stabilizer, or a solubilizer, in accordance with conventional methods. The tablet or pill may be coated with sugar or a film of a substance soluble in the stomach or intestine, as required.

A liquid composition for oral administration is used in the form of a pharmaceutically acceptable emulsion, solution, suspension, syrup or elixir, and contains a generally used inactive diluent, such as purified water or ethanol. The liquid composition may contain, other than the inactive diluent, an auxiliary agent such as a solubilizer, a wetting agent, or a suspending agent, a sweetener, a flavor, an aromatic, or an antiseptic agent.

The injection for parenteral administration contains an aqueous or non-aqueous sterilized solution, suspension or emulsion. Examples of the aqueous solvent include distilled water for injection and physiological saline. Examples of the non-aqueous solvent include propylene glycol, polyethylene glycol, a vegetable oil such as olive oil, an alcohol such as ethanol, and Polysorbate 80. Such compositions may further contain a tonicity agent, a preservative, a wetting agent, an emulsifying agent, a dispersant, a stabilizer, or a solubilizing aid. These are sterilized, for example, by filtration through a bacteria-retention filter, addition of a disinfectant, or irradiation. Alternatively, they can be produced and used by producing a sterilized solid composition, and then dissolving or suspending the solid composition in aseptic water or aseptic solvent for injection just before use.

The external preparation includes an ointment, a plaster, a cream, a jelly, a cataplasm, a spray, a lotion, an eye drop, an eye ointment, and a patch. Such an external preparation contains an ointment base, a lotion base, an aqueous or non-aqueous liquid, a suspension or an emulsion that is generally used. Examples of the ointment base or lotion base include polyethylene glycol, propylene glycol, white petrolatum, white beeswax, polyoxyethylene hydrogenated castor oil, glyceryl monostearate, stearyl alcohol, cetyl alcohol, lauromacrogol, and sorbitan sesquioleate.

In the patch, a non-aqueous base or the like can be used as a carrier. Specific examples thereof include a rubber-based adhesive, an acrylic adhesive, and a silicone adhesive.

Examples of a rubber component of the rubber-based adhesive include a natural rubber, polyisoprene, a styrene-isoprene-styrene block copolymer, a styrene-butadiene-styrene block copolymer, a styrene-butadiene rubber, and polyisobutylene.

The non-aqueous base can further contain a plasticizer, a tackifier, a permeation enhancer, and/or a stabilizer.

The plasticizer is not particularly limited, and examples thereof include a petroleum-based oil (such as paraffinic process oil, naphthenic process oil, or aromatic process oil), squalane, squalene, a vegetable oil (such as olive oil, camellia oil, castor oil, tall oil, or peanut oil), silicone oil, dibasic acid ester (such as dibutyl phthalate, or dioctyl phthalate), a liquid rubber (such as polybutene, or liquid isoprene rubber), a liquid fatty acid ester (such as isopropyl myristate, hexyl laurate, diethyl sebacate, or diisopropyl sebacate), diethylene glycol, polyethylene glycol, glycol salicylate, propylene glycol, dipropylene glycol, triacetin, triethyl citrate, and crotamiton.

The tackifier is not particularly limited, and examples thereof include a rosin derivative (such as rosin, glycerin ester of rosin, hydrogenated rosin, glycerin ester of hydrogenated rosin, pentaerythritol ester of rosin), a cycloaliphatic saturated hydrocarbon resin, an aliphatic hydrocarbon resin, a terpene resin, and a maleic resin.

The permeation enhancer is not particularly limited as long as it is a compound having a recognized permeation-enhancing action in the skin, and specific examples thereof include a fatty acid, an aliphatic alcohol, or a fatty acid ester, amide or ether having 6-20 carbon atoms, an aromatic organic acid, an aromatic alcohol, an aromatic organic acid ester or ether.

As the stabilizer, an antioxidant, a UV absorber, or the like can be used.

Examples of the antioxidant include tocopherol and an ester derivative thereof, ascorbic acid, ascorbic acid stearate, nordihydroguaiaretic acid, dibutyl hydroxytoluene (BHT) and butyl hydroxyanisole. Examples of the UV absorber include a p-aminobenzoic acid derivative, an anthranilic acid derivative, a salicylic acid derivative, a coumarin derivative, an amino acid-based compound, an imidazoline derivative, a pyrimidine derivative and a dioxane derivative.

As an inhalation agent or a transmucosal agent such as a transnasal agent, those in the form of a solid, liquid or semi-solid are used and can be produced by a method known in the art. For example, they may contain a known excipient, a pH adjuster, a preservative, a surfactant, a lubricant, a stabilizer, a thickener, or the like as appropriate. For administration, an appropriate device for inhalation or insufflation can be used. For example, using a known device such as a metered dose inhalation device or spray, a compound may be administered alone or as a formulated mixture in the form of a powder, or as a combination with a pharmaceutically acceptable carrier in the form of a solution or suspension.

A dry powder inhaler or the like may be a device for single administration or multiple administrations and can be used with a dry powder or a powder-containing capsule. Alternatively, the inhaler may be in the form of a pressurized aerosol spray with an ejection agent, for example, a suitable gas such as chlorofluoroalkane, hydrofluoroalkane, or carbon dioxide, etc.

Dosage

In the case of usual oral administration, the dosage per day is about 0.001 to 100 mg/kg, preferably 0.1 to 30 mg/kg, and even more preferably 0.1 to 10 mg/kg body weight, which is administered in a single dose or in two or more doses. In the case of intravenous administration, a suitable dosage per day is about 0.0001 to 10 mg/kg body weight, and administered in a single dose or in a plurality of doses per day. In the case of a transdermal agent, about 0.001 to 100 mg/kg body weight is administered in a single dose or in a plurality of doses per day. The dosage is appropriately and individually determined in consideration of the symptoms, age and sex of the individual, or the like.

Combination Use

In the present invention, the compound of the present invention can be used in combination with various therapeutic or prophylactic agents for diseases for which those agents are believed to be effective. Use of such a combination may be performed by concurrent administration, or by separate administration continuously or at desired intervals. The concurrent administration preparation may be in the form of a combined preparation or separate preparations.

Formulation Example

The patch of the present invention was produced from the following ingredients:
  Active ingredient: Compound of Example 1 10% by weight
  Rubber component of rubber-based adhesive: styrene-isoprene-styrene block copolymer 20% by weight
  Plasticizer: Liquid paraffin 40% by weight
  Tackifier: Rosin 30% by weight The above ingredients were melted and mixed at 150° C., and the dissolved mixture was spread onto a PET film, then the polyester cloth was applied, and the obtained film was cut to the desired size to obtain a patch.

EXAMPLES

Hereinafter, the present invention is described in further detail with reference to Examples and Test Examples, but the present invention is not limited by these.

In the Examples, elution in column chromatography was observed by thin layer chromatography (TLC). In the TLC observation, a silica gel 60F254 manufactured by Merck KGaA was employed as a TLC plate, a solvent used as an eluting solvent in column chromatography was employed as a developing solvent, and a UV detector was employed as a detection method.

The silica gel used for columns was silica gel SK-85 (230 to 400 mesh) manufactured by Merck KGaA, silica gel (Hi-Flash™ Column, INJECT COLUMN™) manufactured by YAMAZEN CORPORATION, silica gel (SNAP, SNAP Ultra) manufactured by Biotage Japan Ltd., or silica gel (FL100B, Chromatrex-SO3H) manufactured by FUJI SILYSIA CHEMICAL LTD. In addition to routine column chromatography, an automated chromatography device (YFLC-5405-FC-GRII, WPrep 2XY) manufactured by YAMAZEN CORPORATION and an automated chromatography device (Isolera, SP-1) manufactured by Biotage Japan Ltd. were used as appropriate. Note that the abbreviations used in the Examples have the following meanings:
  mg: milligram, g: gram, mL: milliliter, MHz: megahertz, Hz: hertz.

In the following Examples, nuclear magnetic resonance (hereinafter referred to as $^1$H-NMR) spectra were obtained by using tetramethylsilane as a standard, and chemical shift values were expressed by δ values (ppm).

Solvents used for measurements were $CDCl_3$: deuterated chloroform, MeOH-$d_4$: deuterated methanol or DMSO-$d_6$: deuterated dimethyl sulfoxide.

For split patterns, a singlet was represented by s, a doublet by d, a triplet by t, a quartet by q, a quintet by quint, a sextet by sext, a septet by hept, a multiplet by m, and broad by br.

Mass spectrometry (hereinafter, MS) was performed by the Atmospheric Pressure Chemical Ionization (APCI) method, Fast Atom Bombardment (FAB) method, Electron Ionization (EI) method, or Electron Spray Ionization (ESI) method. In addition, for some measurements, device models that automatically select and use ESI or APCI as an ionization method for measurement were used.

Example 1

3-[(3R*,4R*)-3-(Dimethylaminomethyl)tetrahydropyran-4-yl]phenol

The configuration in the following formula shows only the relative configuration of the substituents. The compound of this Example is a mixture of two enantiomers.

[Formula 6]

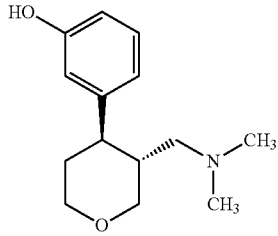

1-a

Methyl 4-(Trifluoromethylsulfonyloxy)-3,6-Dihydro-2H-Pyran-5-Carboxylate

Methyl 4-oxotetrahydropyran-3-carboxylate (20.0 g) was dissolved in anhydrous tetrahydrofuran (800 mL). To this, sodium hydride (7.5 g, 60% mineral oil) was added under ice cooling, and the mixture was stirred for 30 minutes. Comins' reagent (59.5 g) was added and the mixture was stirred at room temperature overnight.

A saturated aqueous ammonium chloride solution was added, and the reaction mixture was diluted with ethyl acetate, and the organic layer was washed with water twice and with saturated saline, and then dried over anhydrous magnesium sulfate. The organic layer was concentrated under reduced pressure and then the residue was purified by silica gel column chromatography (ethyl acetate/n-hexane) to obtain the title compound (30.0 g) as a light yellow oil.
$^1$H-NMR (300 MHz, CDCl$_3$): δ 4.46 (m, 2H), 3.90 (t, J=5.7 Hz, 2H), 3.83 (s, 3H), 2.55 (m, 2H).

1-b

Methyl 4-(3-Methoxyphenyl)-3,6-Dihydro-2H-Pyran-5-Carboxylate

Methyl 4-(trifluoromethylsulfonyloxy)-3,6-dihydro-2H-pyran-5-carboxylate (15.0 g), 3-methoxyphenylboric acid (15.8 g) and potassium carbonate (16.4 g) were suspended in dioxane (300 mL). After nitrogen purge, [1,1'-bis(diphenylphosphino)ferrocene]dichloropalladium (II) (3.80 g) was added, and the mixture was stirred under heating and reflux overnight.

The reaction solution was cooled to room temperature, and then concentrated. The reaction mixture was diluted with ethyl acetate, and the organic layer was washed with water twice and with saturated saline, and then dried over anhydrous magnesium sulfate. The organic layer was concentrated under reduced pressure and then the residue was purified by silica gel column chromatography (ethyl acetate/n-hexane) to obtain the title compound (11.8 g) as a light yellow oil.
$^1$H-NMR (300 MHz, CDCl$_3$): δ 7.28 (t, J=8.4 Hz, 1H), 6.86 (d, J=8.4 Hz, 1H), 6.72-6.77 (m, 2H), 4.46 (m, 2H), 3.89 (m, 2H), 3.82(s, 3H), 3.53 (s, 3H), 2.51 (m, 2H).

1-c

Methyl (3R*,4R*)-4-(3-Methoxyphenyl)Tetrahydropyran-5-Carboxylate

Methyl 4-(3-methoxyphenyl)-3,6-dihydro-2H-pyran-5-carboxylate (11.8 g) was dissolved in a mixed solvent consisting of ethanol (300 mL) and ethyl acetate (60 mL), and after nitrogen purge, 10% palladium carbon (7.0 g, wet) was added.

Under a hydrogen atmosphere (50 psi), the mixture was stirred at room temperature overnight. The reaction mixture was filtered and concentrated under reduced pressure to obtain the title compound (10.6 g) as a light brown oil.
$^1$H-NMR (300 MHz, CDCl$_3$): δ 7.21-7.28 (m, 1H), 6.76-6.89 (m, 3H), 4.18-4.32 (m, 2H), 3.81 (s, 3H), 3.70-3.78 (m, 2H), 3.54 (s, 3H), 3.04-3.10 (m, 1H), 2.72-2.78 (m, 1H), 2.27 (m, 1H), 1.23-1.28 (m, 1H).

1-d

Methyl (3S*,4R*)-4-(3-Methoxyphenyl)Tetrahydropyran-5-Carboxylate

Methyl (3R*,4R*)-4-(3-methoxyphenyl)tetrahydropyran-5-carboxylate (3.50 g) and sodium methoxide (754 mg) were dissolved in anhydrous methanol (100 mL), and the mixture was stirred under heating and reflux overnight. The reaction solution was cooled to room temperature, and then concentrated.

A saturated aqueous ammonium chloride solution was added, and the reaction mixture was diluted with ethyl acetate, and the organic layer was washed with water twice and with saturated saline, and then dried over anhydrous magnesium sulfate. The organic layer was concentrated under reduced pressure to obtain the title compound (2.30 g) as a yellow oil.
$^1$H-NMR (300 MHz, CDCl$_3$): δ 7.20-7.28 (m, 1H), 6.75-6.83 (m, 3H), 4.17-4.21 (m, 1H), 4.06-4.11 (m, 1H), 3.81 (s, 3H), 3.52-3.61 (m, 2H), 3.49 (s, 3H), 2.92-3.06(m, 2H), 1.77-1.89 (m, 2H).

1-e

[(3R*,4R*)-4-(3-Methoxyphenyl)Tetrahydropyran-3-yl]-Methanol

Methyl (3S*,4R*)-4-(3-methoxyphenyl)tetrahydropyran-5-carboxylate (2.20 g) was dissolved in anhydrous tetrahydrofuran (80 mL). Under a nitrogen atmosphere, lithium aluminum hydride (502 mg) was added in portions under ice cooling. The reaction mixture was warmed to room temperature and stirred overnight.

A saturated aqueous ammonium chloride solution was added, and the reaction mixture was extracted with methylene chloride. The organic layer was concentrated under reduced pressure, and then the residue was purified by silica gel column chromatography (ethyl acetate/n-hexane) to obtain the title compound (1.70 g) as a colorless oil.
¹H-NMR (300 MHz, CDCl₃): δ 7.22-7.28 (m, 1H), 6.79-6.84 (m, 3H), 4.21-4.26 (m, 1H), 4.02-4.10 (m, 1H), 3.82 (s, 3H), 3.27-3.55 (m, 4H), 2.54-2.62 (m, 1H), 2.03-2.10 (m, 1H), 1.88-1.93 (m, 1H), 1.72-1.79 (m, 1H).

1-f

Methyl [(3S*,4R*)-4-(3-Methoxyphenyl)Tetrahydropyran-3-yl]-Methanesulfonate

[(3R*,4R*)-4-(3-Methoxyphenyl)tetrahydropyran-3-yl]-methanol (1.80 g) was dissolved in methylene chloride (40 mL), and triethylamine (1.22 g) was added. Under stirring with ice-cooling, methanesulfonyl chloride (2.03 g) was added dropwise. The reaction mixture was warmed to room temperature and stirred for 2 hours.

The reaction mixture was diluted with methylene chloride, and the organic layer was washed with a saturated aqueous ammonium chloride solution and saturated saline, and then dried over anhydrous magnesium sulfate. The organic layer was concentrated under reduced pressure to obtain the title compound (2.40 g) as a yellow oil.

1-g

1-[(3R*,4R*)-4-(3-Methoxyphenyl)Tetrahydropyran-3-yl]-N,N-Dimethyl-Methanamine

Methyl [(3S*,4R*)-4-(3-methoxyphenyl)tetrahydropyran-3-yl]-methanesulfonate (2.40 g) was dissolved in dimethylformamide (15 mL), and dimethylamine hydrochloride (5.40 g) and triethylamine (4.90 g) were added.

The reaction mixture was stirred at 70° C. for 2 days. The mixture was concentrated under reduced pressure, and then the residue was purified by silica gel column chromatography (methanol/methylene chloride) to obtain the title compound (0.20 g) as a white solid.
¹H-NMR (300 MHz, CDCl₃): δ 7.30 (m, 1H), 6.85 (m, 3H), 4.58 (m, 1H), 4.10 (m, 1H), 3.80 (s, 3H) 3.50 (m, 1H), 3.25 (m, 1H), 3.05 (m, 2H), 2.50 (s, 6H), 2.45 (m, 2H), 1.75 (m, 2H).

1-h

3-[(3R*,4R*)-3-(Dimethylaminomethyl)Tetrahydropyran-4-yl]Phenol 1-(3R*,4R*)-4-(3-Methoxyphenyl)tetrahydropyran-3-yl]-N,N-dimethyl-methanamine (2.00 g) was dissolved in methylene chloride (15 mL), and after cooling to −78° C., a solution of 1 M boron tribromide in methylene chloride (6.0 mL) was added dropwise under a nitrogen atmosphere. The reaction mixture was stirred at −78° C. for 3 hours, and then stirred at room temperature overnight.

After methanol (5 mL) was added, the mixture was set to pH 8 with a saturated aqueous sodium bicarbonate solution, and diluted with ethyl acetate, and the organic layer was washed with saturated saline, and then dried over anhydrous magnesium sulfate. The organic layer was concentrated under reduced pressure and then the residue was purified by silica gel column chromatography (ethyl acetate/methanol) to obtain the title compound (60 mg) as a white solid.
¹H-NMR (400 MHz, CDCl₃): δ 7.15-7.19 (t, J=11.6 Hz, 1H), 6.73 (d, J=11.2 Hz, 1H), 6.67-6.70 (m, 2H), 4.30-4.34 (dd, J=11.6 Hz, 3.2 Hz, 1H), 4.03-4.07 (dd, J=11.2 Hz, 3.6 Hz, 1H), 3.45-3.51 (t, J=11.6 Hz, 1H), 3.14-3.19 (t, J=11.6 Hz, 1H), 2.31 (m, 1H), 2.09 (m, 1H), 2.06 (s, 6H), 1.79-1.90 (m, 3H), 1.73 (m, 1H). MS (APCI) m/z: 236 (M+H)⁺.

Example 2

3-[(4R*,5R*)-5-(Dimethylaminomethyl)-2,2-Dimethyltetrahydropyran-4-yl]Phenol

The configuration in the following formula shows only the relative configuration of the substituents. The compound of this Example is a mixture of the two enantiomers.

[Formula 7]

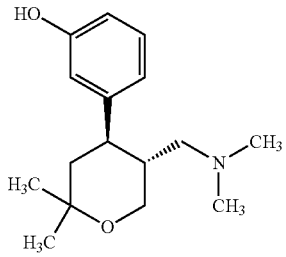

Starting materials, methyl 6,6-dimethyl-4-oxotetrahydropyran-3-carboxylate (11.2 g) and 2-[N,N-bis(trifluoromethanesulfonyl)amino]-5-chloropyridine (30.9 g), were reacted and the resultant was worked up according to the methods of Example 1(1-a) to (1-h) to obtain the title compound (96 mg) as a white solid.
¹H-NMR (400 MHz, CDCl₃): δ 7.15 (t, J=8.0 Hz, 1H), 6.75-6.65 (m, 3H), 4.11 (d, J₁=12.8 Hz, J₂=4 Hz, 1H), 3.48 (t, J=11.6 Hz, 1H), 2.56-2.48 (m, 1H), 2.13-2.00 (m, 8H), 1.94-1.88 (m, 1H), 1.70-1.64 (m, 2H), 1.30 (s, 3H), 1.26 (s, 3H). MS (APCI) m/z: 264 (M+H)⁺.

Example 3

3-[(3R*,4R*)-3-(Dimethylaminomethyl)Tetrahydropyran-4-yl]-5-Methylphenol

The configuration in the following formula shows only the relative configuration of the substituents. The compound of this Example is a mixture of the two enantiomers.

[Formula 8]

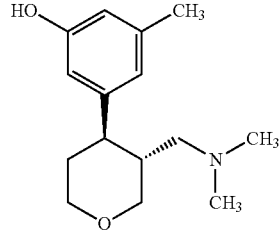

Starting materials, 3-methoxy-5-methylphenylboric acid (3.10 g) and methyl 4-(trifluoromethylsulfonyloxy)-3,6-dihydro-2H-pyran-5-carboxylate (5.40 g), were reacted and the resultant was worked up according to the method of Example 1(1-a) to (1-h) to obtain the title compound (252 mg) as a white solid.

$^1$H-NMR (400 MHz, CD$_3$OD): δ 6.61 (s, 1H), 6.58 (s, 1H), 6.53 (s, 1H), 3.79-3.74 (m, 1H), 3.70-3.65 (m, 1H), 3.59-3.54 (m, 2H), 3.40-3.35 (m, 1H), 3.32 (m, 4H), 3.26 (s, 3H), 3.23-3.21 (m, 1H), 2.56-2.55 (m, 1H), 2.33-2.30 (m, 1H), 2.26 (s, 3H), 2.23-2.20 (m, 1H). MS (APCI) m/z: 250 (M+H)$^+$.

Example 4

3-[(3R*,4R*)-3-(Dimethylaminomethyl)Tetrahydro-pyran-4-yl]-2-Methylphenol

The configuration in the following formula shows only the relative configuration of the substituents. The compound of this Example is a mixture of the two enantiomers.

[Formula 9]

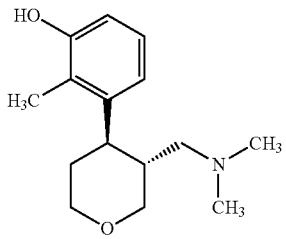

Starting materials, 2-(3-methoxy-2-methylphenyl)-4,4,5,5-tetramethyl-1,3,2-dioxaborolane (6.85 g) and methyl 4-(trifluoromethylsulfonyloxy)-3,6-dihydro-2H-pyran-5-carboxylate (4.00 g), were reacted and the resultant was worked up according to the method of Example 1 (1-a) to (1-h) to obtain the title compound (153 mg) as a white solid.
$^1$H-NMR (400 MHz, CD$_3$OD): δ 7.00 (t, J=7.6 Hz, 1H), 6.77 (d, J=7.6 Hz, 1H), 6.70 (d, J=8.0 Hz, 1H), 3.91 (dd, J$_1$=12.8 Hz, J$_2$=3.2 Hz, 1H), 3.66-3.64 (m, 1H), 3.60-3.52 (m, 4H), 3.17 (dd, J$_1$=11.6 Hz, J$_2$=2.4 Hz, $^1$H), 2.82-2.81 (m, 6H), 2.57-2.52 (m, 2H), 2.21 (s, 3H), 2.04-1.98 (m, 1H). MS (APCI) m/z: 250 (M+H)$^+$.

Example 5

3-[3-Dimethylaminomethyl-4-Fluorotetrahydropy-ran-4-yl]-Phenol

[Formula 10]

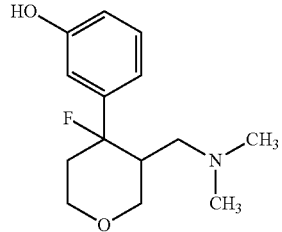

5-a 3-(Dimethylaminomethyl)Tetrahydropyran-4-One

Tetrahydropyran-4-one (20 g), paraformaldehyde (7.00 g), dimethylamine hydrochloride (17.0 g) and 12N hydrochloric acid (0.10 mL) were dissolved in dimethylformamide (100 mL), and the mixture was stirred at 40° C. for 3 hours. The reaction mixture was concentrated under reduced pressure, and to the residue, an ethanol/ethyl acetate mixed solvent was added to precipitate a solid, and then filtration was performed to obtain the solid.
To the obtained solid, methylene chloride (500 mL) and ammonia water were added, and the solution was partitioned. The organic layer was washed with saturated saline (300 mL), and then dried over anhydrous magnesium sulfate. The organic layer was concentrated under reduced pressure to obtain the title compound (14.0 g) as a yellow oil.
$^1$H-NMR (300 MHz, CDCl$_3$): δ 4.17-4.03 (m, 2H), 3.89-3.81 (m, 1H), 3.59-3.53 (m, 1H), 2.76-2.67 (m, 2H), 2.53-2.49 (m, 2H), 2.36-2.28 (m, 1H), 2.19 (s, 6H).

5-b 4-(3-Benzyloxyphenyl)-3-(Dimethylaminomethyl) Tetrahydropyran-4-ol

Pieces of magnesium (0.81 g) were suspended in anhydrous tetrahydrofuran (20 mL), and iodomethane (0.05 mL) and m-bromophenol benzyl ester (9.00 g) were added under a nitrogen atmosphere. The reaction mixture was stirred under heating and reflux for 1 hour. After being cooled to room temperature, the reaction mixture was stirred under ice cooling, and a solution of 3-(dimethylaminomethyl)tetrahydropyran-4-one (4.30 g) in anhydrous tetrahydrofuran (30 mL) was added dropwise, and then the mixture was stirred at room temperature overnight.
Under ice cooling, a saturated aqueous ammonium chloride solution (15 mL) was added, and the organic layer was separated. The aqueous layer was extracted with methylene chloride, the organic layer was combined, and then the mixture was dried over anhydrous magnesium sulfate. The organic layer was concentrated under reduced pressure. To the obtained residue, ethyl acetate (100 mL) was added, and the mixture was reacted with hydrochloric acid gas to precipitate a solid as a hydrochloride salt, and then filtration was performed to obtain the solid.
The obtained solid was washed with ethanol to obtain a light yellow solid (1.50 g). To the obtained solid, ammonia water and methylene chloride were added, and the solution was partitioned. The organic layer was washed with water and dried over anhydrous magnesium sulfate. The organic layer was concentrated under reduced pressure to obtain the title compound (1.50 g) as a white solid.
$^1$H-NMR (400 MHz, CDCl$_3$): δ 7.44 (d, J=7.2 Hz, 2H), 7.38 (t, J=6.8 Hz, 2H), 7.33-7.27 (m, 2H), 7.23 (s, 1H), 7.08 (d, J=7.6 Hz, 1H), 6.70 (dd, J=7.6, 2.4 Hz, 1H), 5.09 (s, 2H), 4.17-4.13 (m, 1H), 4.01 (t, J=12.0 Hz, 1H), 3.85-3.81 (m, 1H), 3.79-3.75 (m, 1H), 2.43-2.39 (m, 1H), 2.17-1.93 (m, 9H), 1.57 (m, 1H).

5-c

1-[4-(3-Benzyloxyphenyl)-4-Fluorotetrahydropyran-3-yl]-N,N-Dimethylaminomethanamine N,N-Diethylaminosulfur trifluoride (163 mg) was dissolved in methylene chloride (5 mL), and under stirring with cooling to −40° C., a solution of 4-(3-benzyloxyphenyl)-3-(dimethylaminomethyl)tetrahydropyran-4-ol (300 mg) in methylene chloride (2 mL) was added dropwise. The reaction mixture was stirred at −40° C. for 2 hours, and warmed to room temperature over 1 hour.

Then, the reaction mixture was cooled to −5° C., and water was added, and the mixture was extracted with methylene chloride. The organic layer was washed with water and saturated saline, and then dried over anhydrous sodium sulfate. The organic layer was concentrated under reduced pressure, and then the residue was purified by silica gel column chromatography (methylene chloride/methanol) to obtain the title compound (110 mg) as a colorless oil.
$^1$H-NMR (400 MHz, CD$_3$OD): δ 7.44-7.42 (m, 2H), 7.38-7.33 (m, 2H), 7.32-7.27 (m, 2H), 7.02-6.99 (m, 1H), 6.97-6.91 (m, 2H), 5.11 (s, 2H), 4.11-4.07 (dd, J=11.6 Hz, 4.8 Hz, 1H), 3.92-3.85 (m, 1H), 3.83-3.74 (m, 1H), 3.55 (t, J=11.6 Hz, 1H), 2.44-2.15 (m, 3H), 2.01(s, 6H), 1.89-1.74 (m, 2H).

5-d

3-[3-Dimethylaminomethyl-4-Fluorotetrahydropyran-4-yl]-Phenol

1-[4-(3-Benzyloxyphenyl)-4-fluorotetrahydropyran-3-yl]-N,N-dimethylaminomethanamine (110 mg) was dissolved in methanol (3 mL), and after nitrogen purge, 10% palladium carbon (55 mg, wet) was added. Under a hydrogen atmosphere (1 atm), the mixture was stirred at room temperature for 2 hours. The reaction mixture was filtered and concentrated under reduced pressure and then purified under the same conditions as in Example 1(1-h) to obtain the title compound (25 mg) as a white solid.
$^1$H-NMR (400 MHz, CD$_3$OD): δ 7.21 (t, J=8.4 Hz, 1H), 6.88-6.79 (m, 2H), 6.76-6.70 (m, 1H), 4.12 (dd, J=12.0, 4.8 Hz, 1H), 3.94-3.86 (m, 1H), 3.85-3.75 (m, 1H), 3.57 (t, J=11.2 Hz, 1H), 2.45-2.11 (m, 3H), 2.05 (s, 6H), 1.93-1.88 (m, 1H), 1.86-1.76 (m, 1H), MS (APCI) m/z: 254 (M+H)$^+$.

Test Example 1

(1) Preparation of Test Sample

The compounds described in the Examples were dissolved or suspended in isopropyl myristate (IPM) at a concentration of 3.84 mmol/L and the resultant was used. The results of the dissolution state in IPM are shown in Table 1.

(2) Hairless Mouse Skin Permeation Test

The frozen skin of a hairless mouse (HR-1 strain, male, 7 weeks old, Japan SLC, Inc.) was thawed at room temperature and, if there was excess subcutaneous fat, the fat was excised with scissors. The horizontal diffusion cell was kept at a constant temperature by flowing water from a thermostatic circulation tank (37° C.) into the external jacket of the cell. The hairless mouse skin was punched out to φ24 mm and mounted tightly in the horizontal diffusion cell, 0.9 mL of a receiver solution (McIlvaine buffer containing 40% polyethylene glycol 400) was added to the dermal side (receiver side), and 0.9 mL of a donor solution (the solution or suspension of the compound described in the Example in IPM at a concentration of 3.84 mmol/L) was added to the stratum corneum side (donor side).

After application of the donor solution, 0.45 mL of liquid was collected from the receiver side when an arbitrary time had elapsed (2, 4, 6, 8, and 24 hours from the application), and an equal amount of fresh receiver solution was added each time. The collected liquid was stored at −80° C. The number of samples in each group was three.

(3) Skin Permeation Test Analysis Method

The compounds in liquids collected in the skin permeation test were quantified. The results obtained were indicated by the mean±S.D. (N=3). The cumulative amount permeated (mmol/cm2)–time (hr) profile was plotted on a graph based on the drug concentration in the liquid on the receiver side obtained at each time point.

Skin permeation rate (flux, mmol/cm2/hr) and Lag time (hr) were calculated from the slope and X-axis intercept, respectively, of the regression line at steady state from the profile, and used as indicators of skin permeation. The results of the skin permeation test are shown in Table 1.

TABLE 1

| Compound | Flux (mmol/cm2/hr) | Dissolution state in IPM |
|---|---|---|
| Example 1 | 35.77 | Dissolved |
| Faxeladol | 17.14 | Suspended |

Faxeladol represents 3-[(1R, 2R)-2-[(dimethylamino) methyl]cyclohexyl]phenol).

(Test Example 2) Evaluation of Analgesic Score by Tail Flick Test in Mice

A Tail Flick analgesic effect metering device (Ugo Basile) and adult mice (C57BL/6JJmsSlc, Japan SLC, Inc.) were used for evaluation. In the Tail Flick test, thermal stimulation was applied to the tail of each animal, and the latency (in seconds) of escape reflection moving the tail was measured. The maximum heat application time was set to 10 seconds in order to prevent burns.

The compounds described in the Examples were dissolved or suspended in Captisol to prepare test samples. Then, test samples at appropriately selected concentrations were administered subcutaneously to the animals (10 mL/kg), and the latency of escape reflection was measured. The latency of escape reflection before test sample administration was set as [pre-dose measurement], and the analgesic score (%) was calculated as [([measurement]−[pre-dose measurement])/(10−[pre-dose measurement])]×100.

The ED50 was determined by calculating a dose with an analgesic score of 50%. The results of this test are shown in Table 2.

TABLE 2

| Compound | ED50 (mg/kg) |
|---|---|
| Example 1 | 1.6 |
| Faxeladol | 2.7 |

In the above two tests, the compound of the present invention exhibited excellent skin permeation and strong analgesic action.

The invention claimed is:

1. A compound of formula (I) or a pharmaceutically acceptable salt thereof:

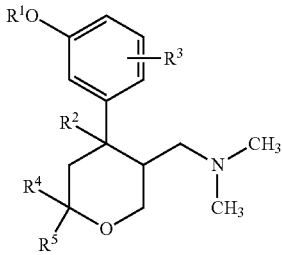

(I)

wherein:
R¹ is a hydrogen atom or a methyl group;
R² is a hydrogen atom or a fluorine atom;
R³ is a hydrogen atom or a methyl group;
R⁴ is a hydrogen atom or a methyl group; and
R⁵ is a hydrogen atom or a methyl group.

2. The compound according to claim 1 or a pharmaceutically acceptable salt thereof, wherein R¹ is a hydrogen atom.

3. The compound according to claim 1 or a pharmaceutically acceptable salt thereof, wherein R² is a hydrogen atom.

4. The compound according to claim 1 or a pharmaceutically acceptable salt thereof, wherein R³ is a hydrogen atom.

5. The compound according to claim 1 or a pharmaceutically acceptable salt thereof, wherein R⁴ and R⁵ are hydrogen atoms.

6. The compound according to claim 1 or a pharmaceutically acceptable salt thereof selected from the group consisting of:
   3-[(3R*,4R*)-3-(Dimethylaminomethyl)tetrahydropyran-4-yl[phenol;
   3-[(4R*,5R*)-5-(Dimethylaminomethyl)-2,2-dimethyltetrahydropyran-4-yl[phenol;
   3-[(3R*,4R*)-3-(Dimethylaminomethyl)tetrahydropyran-4-yl[-5-methylphenol;
   3-[(3R*,4R*)-3-(Dimethylaminomethyl)tetrahydropyran-4-yl[-2-methylphenol;
   3-[3-Dimethylaminomethyl-4-fluorotetrahydropyran-4-yl[-phenol; and
   pharmaceutically acceptable salts thereof.

7. 3-[(3R*,4R*)-3-(Dimethylaminomethyl)tetrahydropyran-4-yl[phenol, or a pharmaceutically acceptable salt thereof.

8. 3-[(3R,4R)-3-(Dimethylaminomethyl)tetrahydropyran-4-yl[phenol, or a pharmaceutically acceptable salt thereof.

9. A pharmaceutical composition comprising the compound according to claim 1 or a pharmaceutically acceptable salt thereof as an active ingredient.

10. The pharmaceutical composition according to claim 9, wherein the composition is in the form of a patch.

11. A method for treating pain in a subject, comprising administering to a subject in need thereof an effective amount of the pharmaceutical composition according to claim 9.

12. The method according to claim 11, wherein the composition is in the form of a patch.

13. The method according to claim 11, wherein the subject is a human.

14. The method according to claim 11, wherein the pain is cancer pain and/or chronic non-cancer pain.

15. A pharmaceutical composition comprising the compound according to claim 7 or a pharmaceutically acceptable salt as an active ingredient.

16. The pharmaceutical composition according to claim 15, wherein the composition is in the form of a patch.

17. A method for treating pain in a subject, comprising administering to a subject in need thereof an effective amount of the pharmaceutical composition according to claim 15.

18. The method according to claim 17, wherein the composition is in the form of a patch.

19. The method according to claim 17, wherein the subject is a human.

20. The method according to claim 17, wherein the pain is cancer pain and/or chronic non-cancer pain.

21. A pharmaceutical composition comprising the compound according to claim 8 or a pharmaceutically acceptable salt as an active ingredient.

22. The pharmaceutical composition according to claim 21, wherein the composition is in the form of a patch.

23. A method for treating pain in a subject, comprising administering to a subject in need thereof an effective amount of the pharmaceutical composition according to claim 21.

24. The method according to claim 23, wherein the composition is in the form of a patch.

25. The method according to claim 23, wherein the subject is a human.

26. The method according to claim 23, wherein the pain is cancer pain and/or chronic non-cancer pain.

* * * * *